United States Patent
Goto et al.

(10) Patent No.: US 9,435,006 B2
(45) Date of Patent: Sep. 6, 2016

(54) EXTRACTION AGENT FOR PRECIOUS METALS AND RHENIUM, AND EXTRACTION METHOD FOR PRECIOUS METALS AND RHENIUM USING SAME

(71) Applicants: Kyushu University, National University Corporation, Fukuoka (JP); SUMITOMO METAL MINING CO., LTD., Tokyo (JP)

(72) Inventors: Masahiro Goto, Fukuoka (JP); Fukiko Kubota, Fukuoka (JP); Yuzo Baba, Fukuoka (JP)

(73) Assignees: Kyushu University, National University Corporation, Fukuoka-Shi (JP); SUMITOMO METAL MINING CO., LTD., Tokyo (JP)

( * ) Notice: Subject to any disclaimer, the term of this patent is extended or adjusted under 35 U.S.C. 154(b) by 0 days.

(21) Appl. No.: 14/779,908

(22) PCT Filed: Apr. 8, 2014

(86) PCT No.: PCT/JP2014/060211
§ 371 (c)(1),
(2) Date: Sep. 24, 2015

(87) PCT Pub. No.: WO2014/171370
PCT Pub. Date: Oct. 23, 2014

(65) Prior Publication Data
US 2016/0047012 A1 Feb. 18, 2016

(30) Foreign Application Priority Data

Apr. 15, 2013 (JP) .................................. 2013-085000
Apr. 8, 2014 (JP) .................................. 2014-079153

(51) Int. Cl.
*C22B 11/00* (2006.01)
*C22B 3/20* (2006.01)
(Continued)

(52) U.S. Cl.
CPC .............. *C22B 11/04* (2013.01); *C07C 237/06* (2013.01); *C22B 3/0024* (2013.01); *C22B 3/20* (2013.01); *C22B 61/00* (2013.01); *Y02P 10/234* (2015.11)

(58) Field of Classification Search
CPC ......... C22B 11/04; C22B 3/20; C22B 61/00; C07C 237/06
See application file for complete search history.

(56) References Cited

U.S. PATENT DOCUMENTS 5,326,760 A * 7/1994 McElroy ............... C07C 237/06
514/235.2
6,365,049 B1 4/2002 Smith
(Continued)

FOREIGN PATENT DOCUMENTS

EP 2679693 A1 1/2014
JP H07-286221 A 10/1995
(Continued)

OTHER PUBLICATIONS

Extended European Search Report dated Feb. 3, 2016, issued for European Patent Application No. 14785986.2.
(Continued)

*Primary Examiner* — George Wyszomierski
*Assistant Examiner* — Tina M McGuthry Banks
(74) *Attorney, Agent, or Firm* — Locke Lord LLP; James E. Armstrong, IV; Nicholas J. DiCeglie, Jr.

(57) ABSTRACT

The present invention extracts precious metals from an acidic solution containing precious metals in an early and highly efficient manner. Provided is an extraction agent for precious metals that is represented by the general formula below. In the formula, R1 and R2 each represent the same alkyl group or different alkyl groups, R3 represents a hydrogen atom or an alkyl group, and R4 represents a hydrogen atom or a discretionary group that is not an amino group and that bonds to α carbon as an amino acid. By subjecting an acidic solution containing precious metals to solvent extraction using the extraction agent for precious metals, a plurality of precious metals can be recovered all at once from a solution containing a large amount of various impurities.

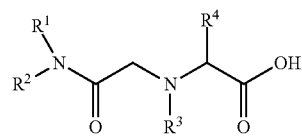

12 Claims, 5 Drawing Sheets (51) Int. Cl.
    *C22B 61/00*  (2006.01)
    *C07C 237/06* (2006.01)
    *C22B 3/00*   (2006.01)
    *C22B 3/32*   (2006.01)

(56) References Cited

U.S. PATENT DOCUMENTS

2013/0102806 A1  4/2013  Sakaki et al.
2014/0328737 A1  11/2014  Goto et al.

FOREIGN PATENT DOCUMENTS

| | | |
|---|---|---|
| JP | 2001-098335 A | 4/2001 |
| JP | 2012-012371 A | 1/2012 |
| JP | 2012-167367 A | 9/2012 |
| JP | 2013032563 A | 2/2013 |
| WO | WO-2013-069562 | 5/2013 |

OTHER PUBLICATIONS

International Search Report for PCT/JP2014/060211 dated Jul. 8, 2014.

Robert Pajewski et al, "The effect of midpolar regime mimics on anion transport mediated by amphiphilic heptapeptides," New Journal of Chemistry, 2007, vol. 31, pp. 1960-1972.

Office Action dated Feb. 3, 2016, issued for Chinese Patent Application No. 201480019608.7.

\* cited by examiner

FIG. 1

¹H-NMR SPECTRUM OF A SAMPLE

<MEASUREMENT CONDITIONS>
SAMPLE CONCENTRATION : APPROX. 30 wt% / $CDCl_3$ SOLUTION
NUMBER OF SCANS : 128
BASE PEAK : 1H OF $CHCl_3$ IN $CDCl_3$ ($\delta$ =7.27ppm)

Relationship between pH and extraction rates of various metals when extraction agent of example is used

FIG. 5

Relationship between pH and extraction rates of impurities when extraction agent of example is used

EXTRACTION AGENT FOR PRECIOUS METALS AND RHENIUM, AND EXTRACTION METHOD FOR PRECIOUS METALS AND RHENIUM USING SAME

CROSS-REFERENCE TO RELATED APPLICATIONS

This application is the national phase under 35 U.S.C. §371 of PCT International Application No. PCT/JP2014/060211, filed Apr. 8, 2114, which claims the benefit of Japanese Application No. 2013-085000, filed Apr. 15, 2013, and Japanese Application No. 2014-079153, filed Apr. 8, 2014, the entire contents of the aforementioned applications are hereby incorporated herein by reference.

TECHNICAL FIELD

The present invention relates to an extraction agent for precious metals and rhenium, and an extraction method for precious metals and rhenium using the extraction agent.

BACKGROUND ART

Gold, silver, and elements of the platinum group are known as valuable precious metals and are used not only as jewelry and currency but also in various industrial applications. The elements of the platinum group include platinum, palladium, rhodium, ruthenium, iridium, osmium, and the like. Rhenium, which is usually not categorized as a precious metal but is an industrially valuable metal as well, is also a scarce and expensive metal.

For example, gold is used in bonding wires for semiconductor integrated circuits and in contact materials for electronic substrates. Silver is used in photography films and conductive paste. Platinum, palladium, and rhodium are used in catalysts, electrode materials, temperature sensors, medical equipment, and electronic materials. Rhenium is used as thermocouple, catalysts, and the like.

Being scarce and expensive, gold, silver, the elements of the platinum group, and rhenium (hereinafter in the present invention, these are collectively called "precious metals") are obtained by collecting and recycling used products, defective products yielded during manufacturing processes, and the like. Employed as a method of recycling precious metals are a dry process of melting and separating in a furnace at a high temperature and a wet process of melting in acid and the like and then separating by a method such as neutralization, solvent extraction, crystallization, and electrowinning. The dry process has advantages of having excellent productivity to treat a large quantity in a single process and requiring no additional separation step, but it also has a problem in the retrieval rate in retrieving precious metals, namely, loss of precious metals. On the other hand, the wet process has an advantage in terms of its capability of retrieving with little loss of precious metals, but it also has a problem that retrieval of precious metals at high purity is accompanied by challenging separation from other coexisting components. Because of these, retrieval is carried out by considering the advantages of both processes and adopting either the dry process or the wet process, or both of these in combination.

As the wet process, various techniques are developed. For example, Patent Document 1 describes a method of retrieving platinum group metals at high purity from raw material containing the platinum group metals. Specifically, elements of the platinum group are sequentially separated and retrieved according to the following procedure. By the method described in Patent Document 1, the metal Pd having purity of 99.95% can be retrieved at a percent yield of 99%.

(1) A smelting residue is subjected to chlorination with hydrochloric acid and hydrogen peroxide, to give 3 L of a chlorination solution (A). The amount of hydrochloric acid added is determined so as to achieve a concentration of free hydrochloric acid in this solution of 4 mol/L or higher.

(2) The solution containing the elements of the platinum group (the chlorination solution A) is mixed with 1 L of DBC (dibutyl carbitol) for 30 minutes to extract gold.

(3) Caustic soda is added to the residual solution after gold extraction, followed by neutralization until the concentration of free hydrochloric acid reaches 2 mol/L. The resultant neutralized solution (the residual solution after Au extraction) at a volume of 3 L and 3 L of DHS (dihexyl sulphide) are mixed for 3 hours to extract palladium (Pd).

(4) The Pd-containing DHS resulting from the above step (3) is washed with 3 L of hydrochloric acid (concentration: 1 mol/L) and, thereto, 3 L of an aqueous solution of ammonia and ammonium chloride ($NH_3$ concentration: 3 mol/L, $NH_4Cl$ concentration: 1 mol/L) is added for back extraction of Pd. To the aqueous solution containing Pd as a result of back extraction, hydrochloric acid is added to achieve a pH of lower than 1, so that Pd yellow is retrieved. The resultant Pd yellow is dissolved in an aqueous ammonia solution, and to the resultant solution, hydrazine is added for reduction.

Patent Document 1: Japanese Unexamined Patent Application, Publication No. 2012-167367

DISCLOSURE OF THE INVENTION

Problems to be Solved by the Invention

When recycling from scrap, smelting ore, and the like, the content of impurities is usually higher than the content of precious metals and accordingly the precious metals alone need to be separated from a solution containing various impurities at a high proportion. Similarly in Patent Document 1, precious metals are separated from an acid solution of hydrochloric acid in which a smelting residue is dissolved (a chlorination solution A). On the other hand, precious metals are expensive, and therefore the burden of interest generated during the process spanning from the delivery of raw material until the products are sent out is too high to neglect compared to when retrieving other metals. For this reason, retrieval of precious metals from a solution containing various impurities at a high proportion needs to be achieved with high efficiency in a short period of time.

In the technique described in Patent Document 1, however, the gold extraction solution is prepared from the chlorination solution using the first extraction solvent (DBC: dibutyl carbitol) (step (2) above) and then the palladium extraction solution is prepared from the residual solution after gold extraction by using the second extraction solvent (DHS: dihexyl sulphide) (step (3) above). Therefore, in this technique, a process of precious metal extraction needs to be repeated as many times as the number of different kinds of precious metals to be retrieved. Also, in this technique, the yield of extraction solution is substantially the same as the amount of a crude solution (a chlorination solution), after being multiplied by the number of different kinds of precious metals to be retrieved. Furthermore, actual operation of the technique described in Patent Document 1 requires many production facilities and a corresponding capital investment, and therefore development of a technique to retrieve precious metals with even higher efficiency in an even shorter period of time is demanded.

An object of the present invention is to provide an extraction agent that allows early and highly efficient extraction of precious metals from an acid solution containing the precious metals and an extraction method for precious metals using the extraction agent.

Means for Solving the Problems

As a result of repeated intensive investigation to solve the above problem, the present inventors found that provision of a precious metal extraction agent that contains an amide derivative represented by the following general formula (I) makes it possible to retrieve a plurality of kinds of precious metals in a single process from a solution containing various impurities at a high proportion, thereby completing the present invention. Specifically, the present invention provides as follows.

(1) The present invention is a precious metal extraction agent that comprises an amide derivative represented by the following general formula (I):

(I)

(wherein, $R^1$ and $R^2$ each represent the same or different alkyl groups;
the alkyl group can be a straight chain or a branched chain;
$R^3$ represents a hydrogen atom or an alkyl group; and
$R^4$ represents a hydrogen atom or any group other than an amino group, which is bound to the α carbon as an amino acid).

(2) The present invention is also the precious metal extraction agent according to (I), in which the amide derivative is any one or more of glycinamide derivatives, histidinamide derivatives, lysinamide derivatives, aspartamide derivatives, and N-methylglycine derivatives.

(3) The present invention is also an extraction method for precious metals, the method comprising subjecting an acid solution containing precious metals to solvent extraction with the precious metal extraction agent according to (1) or (2) to extract the precious metals from the acid solution.

(4) The present invention is also the extraction method for precious metals according to any one of (1) to (3), in which the acid solution is subjected to the solvent extraction with the pH of the acid solution adjusted to 0.8 or higher and 3.5 or lower.

(5) The present invention is also the extraction method for precious metals according to any one of (1) to (3), in which the acid solution contains the precious metals and at least one or more of manganese, nickel, and/or cobalt, and the acid solution is subjected to the solvent extraction with the pH of the acid solution adjusted to 2.5 or lower.

(6) The present invention is also a palladium separation method, the method comprising:
employing the extraction method for precious metals according to any one of (3) to (5), to the extraction agent in which the precious metals have been extracted from the acid solution, adding a second acid solution having a pH lower than the pH of the acid solution, and mixing the resultant to carry out back extraction, and separating the extraction agent from the second acid solution to separate palladium from other precious metals.

(7) The present invention is also a rhenium separation method, the method comprising:
employing the extraction method for precious metals according to any one of (3) to (5), to the extraction agent in which the precious metals have been extracted from the acid solution, adding a second acid solution having a pH lower than the pH of the acid solution, and mixing the resultant to carry out back extraction, and separating the extraction agent from the second acid solution to separate rhenium from other precious metals.

(8) The present invention is also a rhodium separation method, the method comprising subjecting an acid solution containing rhodium and at least one or more of platinum, osmium, iridium, and palladium to solvent extraction with the precious metal extraction agent according to (1) or (2) with the pH of the acid solution adjusted to 2.5 or lower, to separate the rhodium from other metals.

(9) The present invention is also an iridium separation method, the method comprising:
subjecting an acid solution containing iridium and at least one or more of osmium and ruthenium to solvent extraction with the precious metal extraction agent according to (1) or (2), adding, thereto, a second acid solution that is the acid solution having a pH adjusted to 1.5 or lower, and mixing the resultant to carry out back extraction, and separating the extraction agent from the second acid solution to separate iridium from osmium and ruthenium.

Effects of the Invention

According to the present invention, a plurality of kinds of precious metals can be retrieved in a single process from an acid solution containing various impurities at a high proportion. In other words, the steps (2) and (3) described in Patent Document 1 can be carried out in a single process. As a result, only a single step is required to extract the precious metals from the acid solution and therefore the volume of the extraction solution can be significantly reduced. Accordingly, the production facilities can be small, and early and highly efficient extraction of the precious metals from the acid solution containing the precious metals is possible.

PREFERRED MODE FOR CARRYING OUT THE INVENTION

The specific embodiments of the present invention will now be described in detail. It should be noted, however, that the present invention is not restricted to the following embodiments and can be carried out with proper modification within the scope of the object of the invention. Usually, rhenium is not categorized as a precious metal. However, rhenium can also be excellently extracted with the extraction agent of the present invention and by the extraction method of the present invention and therefore, as described above, can be handled in the same manner as the way precious metals in a narrow sense are handled.

Precious Metal Extraction Agent

The precious metal extraction agent of the present invention comprises an amide derivative represented by the following general formula (I):

In the formula, substituents $R^1$ and $R^2$ each represent the same or different alkyl groups. The alkyl group can be a straight chain or a branched chain. $R^3$ represents a hydrogen atom or an alkyl group. $R^4$ represents a hydrogen atom or any group other than an amino group, which is bound to the α carbon as an amino acid. In the present invention, lipophilicity is increased by introducing alkyl groups into the amide skeleton, and the compound can be used as an extraction agent.

The above amide derivative is any one or more of glycinamide derivatives, histidinamide derivatives, lysinamide derivatives, aspartamide derivatives, and N-methylglycine derivatives. When the amide derivative is a glycinamide derivative, the above glycinamide derivative can be synthesized by the following method. First, a 2-halogenated acetyl halide is added to an alkylamine having a structure represented by $NHR^1R^2$ ($R^1$ and $R^2$ are the same as the above substituents $R^1$ and $R^2$), and the hydrogen atom of amine is substituted with a 2-halogenated acetyl by the nucleophillic substitution reaction to obtain a 2-halogenated (N,N-di)alkylacetamide.

Next, the above 2-halogenated (N,N-di)alkylacetamide is added to glycine or an N-alkylglycine derivative, and one of the hydrogen atoms of the glycine or N-alkylglycine derivative is substituted with an (N,N-di)alkylacetamide group by the nucleophillic substitution reaction. A glycine alkylamide derivative can be synthesized by the two-step reactions.

A histidinamide derivative, a lysinamide derivative or an aspartamide derivative can be synthesized by substituting glycine with histidine, lysine or aspartic acid. The extraction behavior of lysine and aspartic acid derivatives is, however, thought to be within the range of the results obtained by using a glycine derivative and a histidinamide derivative according to the complex stability constant of manganese, cobalt and the like, which are targets.

Extraction Method for Precious Metals

To extract precious metal ions using an extraction agent synthesized by the above method, with an acid aqueous solution comprising the objective precious metal ions being adjusted, the acid aqueous solution is added to an organic solution of the above extraction agent, and mixed. Therefore, the objective precious metal ions can be selectively extracted in the organic phase.

The organic solvent after extraction of the precious metal ions is collected, and to this, a starting solution for back extraction is added and stirred to separate the objective precious metal ions by extraction to an organic solvent, with the starting solution adjusted to a pH lower than that of the above acid aqueous solution. The objective precious metal ions can be further retrieved from the organic solvent in an aqueous solution by back extraction of the objective precious metal ions. As a solution for back extraction, for example, an aqueous solution in which nitric acid, hydrochloric acid or sulphuric acid is diluted is suitably used. In addition, the objective precious metal ions can be concentrated by suitably changing the ratio of the organic phase and the aqueous phase.

Any organic solvent can be used, as long as an extraction agent and the extracted species of metals are dissolved with the solvent, and examples thereof include chlorine-based solvents such as chloroform and dichloromethane, aromatic hydrocarbons such as benzene, toluene and xylene, aliphatic hydrocarbons such as hexane, and the like. These organic solvents can be used individually, or two or more organic solvents can be mixed, and alcohols such as 1-octanol can be mixed therewith.

The concentration of the extraction agent can be properly set depending on the types and concentrations of precious metals. In addition, the equilibrium arrival time varies depending on the types and concentrations of precious metals and the amounts of extraction agent to be added, and thus the stirring time and extraction temperature can be suitably set depending on the conditions of an acid aqueous solution of precious metal ions and an organic solution of the extraction agent. The pH of an acid aqueous solution comprising metal ions can be also suitably adjusted depending on the types of precious metal.

[Extraction of Precious Metals]

In order to efficiently extract precious metals from an acid aqueous solution containing the precious metals, any of the amide derivatives above may be used as an extraction agent.

At the time of extraction, the pH can be within a wide range from a highly acidic region of about 0.8 to a weakly acidic region of 3.5 or higher. When the acid aqueous solution containing precious metals also contains impurities, the organic solution of the extraction agent is preferably added with the pH adjusted to a pH range where little impurities are extracted. For example, when the impurities contain manganese, extraction can be carried out at a pH within the wide pH range described above from a highly acidic region of about 0.8 to a weakly acidic region of 3.5 or higher. When the impurities contain cobalt, the pH is preferably 3.0 or lower and is more preferably 2.5 or lower. When the impurities contain nickel, the pH is preferably 2.5 or lower and is more preferably 2.0 or lower.

The lower limit to the pH is not particularly limited. However, because back extraction of precious metals proceeds when an acid at a high concentration Is mixed, and because general knowledge is that deterioration of an extraction agent that is an organic substance is promoted by an acid, the pH at the time of extraction is preferably about 1 or higher and is more preferably 1.5 or higher.

It should be noted that the extraction agent of the present invention displays a characteristic behavior that, at the pH range from 1 to 1.5, among the elements of the platinum group, platinum, palladium, osmium, and the like are excellently extracted but rhodium is not extracted. Taking advantage of such a difference in characteristics, it is possible to extract, from an acid solution containing the platinum group metal components, the platinum group metal components except for rhodium at the pH range described above and therefore separate them from rhodium.

It should also be noted that, as for rhenium, osmium, iridium, and ruthenium extracted into the extraction agent, back extraction with a 3-M hydrochloric acid solution, for example, retrieves 56% of the extracted rhenium and 73% of the extracted iridium but retrieves as little as lower than 1% of each of the extracted ruthenium and the extracted osmium. Taking advantage of such characteristics, iridium can be effectively separated from osmium and ruthenium.

The mechanism in which the extraction agent of the present invention exhibits an extraction behavior different from the extraction behaviors of conventional extraction agents is not accurately grasped. However, it is thought that the structural characteristics of the extraction agent of the present invention give rise to effects that conventional extraction agents do not have.

It should be noted that by adding, to the extraction agent after extraction, a second acid solution having a pH lower than the pH of the acid solution used in the previous step, mixing the resultant to carry out back extraction, and subsequently separating the extraction agent from the acid solution, palladium can be retrieved. In addition, gold can be retrieved through electrowinning of the back extraction solution, for example. Platinum can be retrieved by adding a reducing agent such as hydrazine. Silver can be retrieved by blowing gas such as sulphur dioxide thereinto for reduction.

EXAMPLES

The present invention will now be described in more detail by way of examples. It should be noted, however, that the present invention is not restricted to these descriptions.

Example

As an example of amide derivatives forming an extraction agent, a glycinamide derivative represented by the following general formula (I) was synthesized, that is, N—[N,N-bis(2-ethylhexyl)aminocarbonylmethyl]glycine (or also referred to as N,N-di(2-ethylhexyl)acetamide-2-glycine, hereinafter referred to as "D2EHAG"), into which two 2-ethylhexyl groups were introduced.

D2EHAG was synthesized as follows. First, as shown in the following reaction formula (II), 23.1 g (0.1 mol) of commercially available di(2-ethylhexyl)amine and 10.1 g (0.1 mol) of triethylamine were collected. These were dissolved by adding chloroform, and 13.5 g (0.12 mol) of 2-chloroacetyl chloride was then added by drops thereto, followed by washing with 1 mol/l hydrochloric acid once. After this, washing was carried out with ion exchanged water and the chloroform phase was collected. Next, anhydrous sodium sulphate was added in a suitable amount (approximately 10 to 20 g) for dehydration, followed by filtration to obtain 29.1 g of yellow liquid. When the structure of this yellow liquid (reaction product) was identified using a nuclear magnetic resonance spectrometer (NMR), the above yellow liquid was confirmed to have the structure of 2-chloro-N,N-di(2-ethylhexyl)acetamide (hereinafter referred to as "CDEHAA"). The percent yield of CDEHAA was 90% relative to di(2-ethylhexyl)amine, a raw material.

Figure 1:
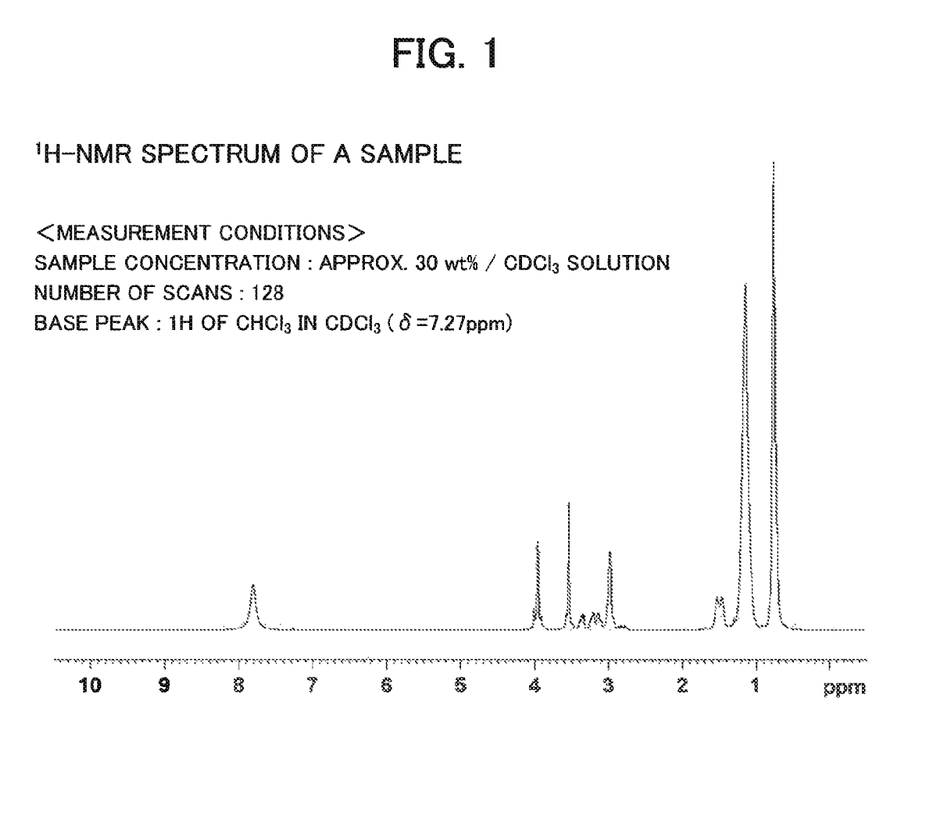
FIG. 1 is a figure showing a $^1$H-NMR spectrum of a glycinamide derivative synthesized in the example of the present invention.
Figure 2:
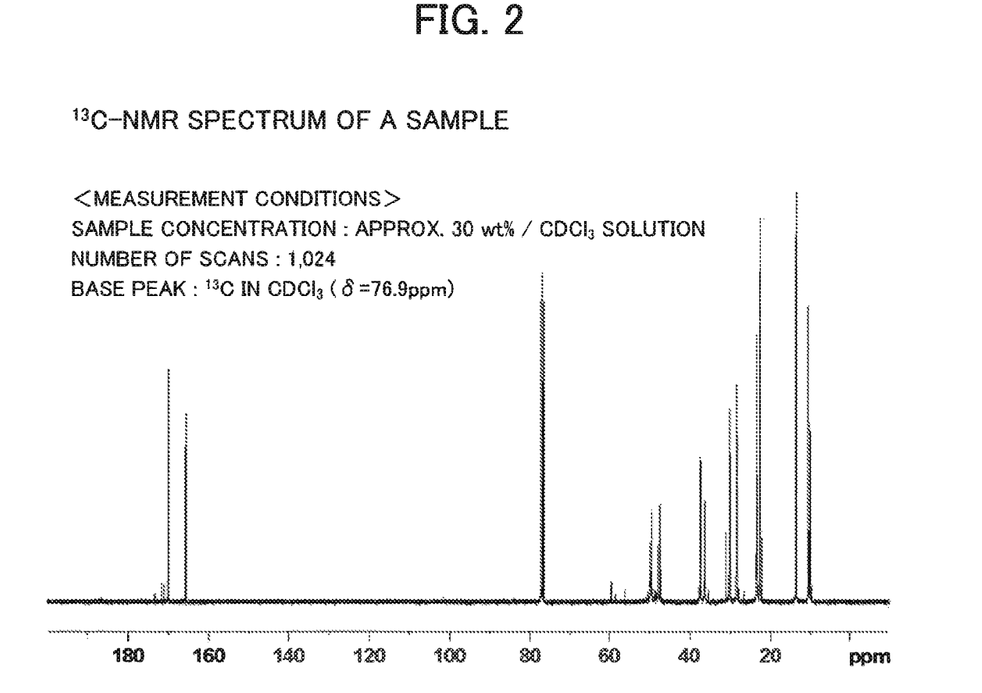
FIG. 2 is a figure showing a $^{13}$C-NMR spectrum of a glycinamide derivative synthesized in the example of the present invention.

Next, as shown in the following reaction formula (III), 8.0 g (0.2 mol) of sodium hydroxide was dissolved by adding methanol, and 15.01 g (0.2 mol) of glycine was further added thereto. While stirring the obtained solution, 12.72 g (0.04 mol) of the above CDEHAA was slowly added dropwise thereto and stirred. After completion of stirring, the solvent in the reaction liquid was distilled off, and the residue was dissolved by adding chloroform. To this solution, 1 mol/l of sulphuric acid was added for acidification, followed by washing with ion exchanged water, and the chloroform phase was collected. To this chloroform phase, anhydrous magnesium sulphate was added in a suitable amount for dehydration, followed by filtration. The solvent was removed under reduced pressure again to obtain 12.5 g of a yellow paste. The percent yield based on the amount of the above CDEHAA was 87%. When the structure of the yellow paste was identified by NMR and elemental analysis, the paste was confirmed to have the structure of D2EHAG, as shown in FIG. 1 and FIG. 2. The above steps were carried out to obtain a precious metal extraction agent of the example of the present invention.

D2EHAG

Comparative Example

In a comparative example, N,N-dioctyl-3-oxapentan-1,5-amic acid (hereinafter referred to as "DODGAA") was used.

Synthesis of DODGAA was carried out as follows. First, as shown by the following reaction formula (VI), 40 ml of dichloromethane was added to a round-bottom flask that contained 4.2 g of diglycolic anhydride, and the resultant was suspended. Thereto, 7 g of dioctylamine (purity: 98%) dissolved in 10 ml of dichloromethane was slowly added through a tap funnel. The resultant solution was stirred at room temperature, and when it was confirmed that the reaction of diglycolic anhydride proceeded enough to make the solution transparent, the reaction was terminated.

(VI)

Then, the solution was washed with water to remove water-soluble impurities. To the solution after washing with water, sodium sulphate was added as a dehydrator. The resultant solution was suction-filtered, and then solvent was evaporated off. This was followed by recrystallization with the use of hexane (3 times) and then vacuum drying. The yield of the resultant substance was 9.57 g, and the percent yield based on the amount of the above diglycolic anhydride was 94.3%. When the structure of the resultant substance was identified by NMR and elemental analysis, the resultant substance was confirmed to be DODGAA at a purity 99% or higher.

Extraction of Gold, Platinum Group Metals, and Rhenium

Extraction and separation of precious metals were performed using the extraction agent of the example of the present invention (D2EHAG) and the extraction agent of the comparative example of the present invention (DODGAA).

[Extraction and Separation of Gold, Platinum, and Palladium]

Several types of acid solutions of hydrochloric acid comprising typical precious metals, namely, gold, platinum, and palladium each in an amount of $1 \times 10^{-4}$ mol/l and being adjusted to pH 0.8 to 10.3 were prepared for use as crude liquids. The crude liquid and an equal volume of an N-dodecane solution comprising 0.01 mol/l of a precious metal extraction agent were added together in test tubes, and the test tubes were put into a constant temperature oven at 25° C. and shaken for 24 hours. At this time, the pH of the hydrochloric acid solution was adjusted using hydrochloric acid at a concentration of 0.1 mol/l and a sodium hydroxide solution at a concentration of 1 mol/l.

After shaking, the aqueous phase was collected, and the gold concentration, the platinum concentration, and the palladium concentration were measured using inductively coupled plasma-atomic emission spectroscopy (ICP-AES). Other platinum group metals such as rhodium, osmium, and iridium and silver are thought to exhibit a behavior the same as or similar to the behavior of the components of the example of the present invention.

The organic phase was subjected to back extraction using 1 mol/l hydrochloric acid. The gold concentration, the platinum concentration, and the palladium concentration in the back extraction phase were measured using ICP-AES.

Figure 3:
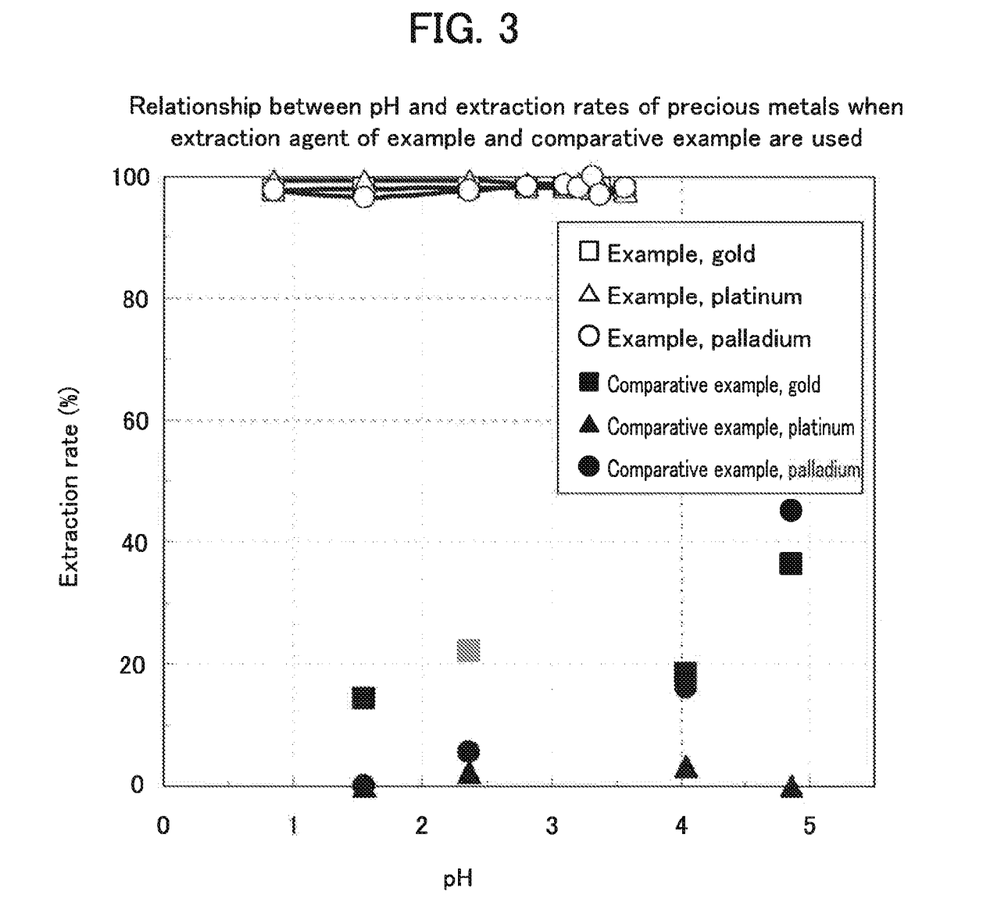
FIG. 3 shows the results of extraction of gold, platinum, and palladium from an acid solution containing precious metals with the use of a precious metal extraction agent of the example of the present invention.

From these measurement results, the extraction rates of gold, platinum, and palladium were defined as (1−concentration after extraction/concentration before extraction)×100 and measured. The results are shown in FIG. 3. In FIG. 3, the abscissa is the pH of an acid solution of hydrochloric acid after extraction, and the ordinate is the extraction rate of gold, platinum, or palladium.

In FIG. 3, white squares indicate the extraction rate of gold when the extraction agent of the example of the present invention was used, white triangles indicate the extraction rate of platinum when the extraction agent of the example of the present invention was used, and white circles indicate the extraction rate of palladium when the extraction agent of the example of the present invention was used. On the other hand, black squares indicate the extraction rate of gold when the extraction agent of the comparative example of the present invention was used, black triangles indicate the extraction rate of platinum when the extraction agent of the comparative example of the present invention was used, and black circles indicate the extraction rate of palladium when the extraction agent of the comparative example of the present invention was used.

With the use of the precious metal extraction agent of the example of the present invention, the extraction rates of gold, platinum, and palladium exceeded 95% even at a pH within a highly acidic region of about 1.0.

A sample of the extraction agent of the example of the present invention (organic phase) in which gold, platinum, and palladium were extracted and that had pH 1.6 was mixed with the same volume of a hydrochloric acid solution at a concentration of 5 mol/l, followed by back extraction (not shown). The back extraction rates were 10.5% for gold, 22.4% for platinum, and 89.4% for palladium. This result shows that by adding, to the extraction agent after extraction, a second acid solution having a pH lower than the pH of the acid solution used in the previous step, mixing the resultant to carry out back extraction, and subsequently separating the extraction agent from the acid solution, palladium can be retrieved.

Instead, with the use of the extraction agent of the comparative example of the present invention, the efficiency in extraction of precious metals within an acidic region was not as high as when the extraction agent of the example of the present invention was used.

[Extraction and Separation of Osmium, Rhodium, Iridium, Ruthenium, and Rhenium]

Solvent extraction and back extraction of an organic phase with the use of the precious metal extraction agent of the example of the present invention (D2EHAG) were performed in the same manner as in the procedure described in [Extraction and separation of gold, platinum, and palladium] except that several types of acid solution of hydrochloric acid comprising osmium, rhodium, iridium, ruthenium, and rhenium each in an amount of $1 \times 10^{-4}$ mol/l and being adjusted to pH 0 to 1.2 were prepared for use as crude liquids. The concentrations of various metals in the back extraction phase were measured using ICP-AES.

Figure 4:
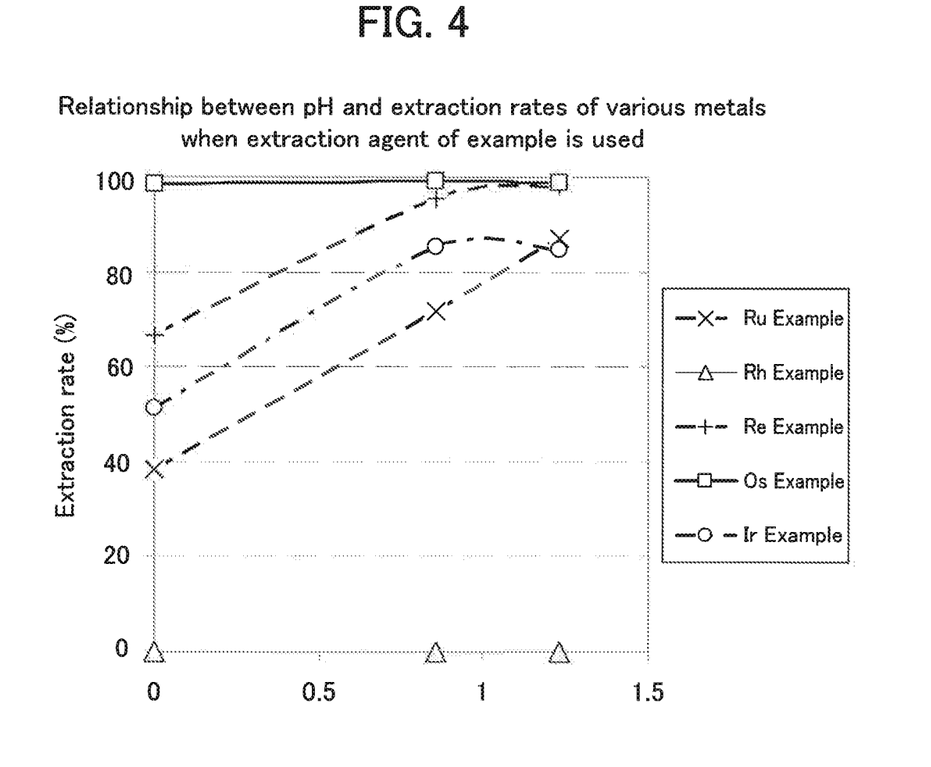
FIG. 4 shows the results of extraction of osmium, rhodium, iridium, ruthenium, and rhenium from an acid solution containing osmium, rhodium, iridium, ruthenium, and rhenium with the use of a precious metal extraction agent of the example of the present invention.

From these measurement results, the extraction rates of osmium, rhodium, iridium, ruthenium, and rhenium were defined as (1−concentration after extraction/concentration before extraction)×100 and measured. The results are shown in FIG. 4. In FIG. 4, the abscissa is the pH of an acid solution of hydrochloric acid after extraction, and the ordinate is the extraction rate of osmium, rhodium, iridium, ruthenium, or rhenium.

In FIG. 4, white squares indicate the extraction rate of osmium when the extraction agent of the example of the present invention was used, white triangles indicate the extraction rate of rhodium when the extraction agent of the example of the present invention was used, and white circles indicate the extraction rate of iridium when the extraction agent of the example of the present invention was used. The symbols "x" indicate the extraction rate of ruthenium when the extraction agent of the example of the present invention was used, and the symbols "+" indicate the extraction rate of rhenium when the extraction agent of the example of the present invention was used.

As for rhenium, iridium, and ruthenium, the extraction rates were about 40 to 70% at near pH 0, and once the pH exceeded 1, the extraction rates started to exceed 80%. Such extraction rates are industrially applicable with no problem. As for osmium, the extraction rate was 95% or higher within a highly acidic region at near pH 0. Accordingly, particularly in separating rhenium, iridium, and ruthenium from a solution containing impurities such as nickel and cobalt, extraction performed at a pH between 1 and 2 can enhance efficiency of separation from the impurities while maintaining a high extraction rate.

On the other hand, no rhodium was extracted in the example of the present invention at a pH within the range from 0 to 1.2.

Extraction of Impurities (Manganese, Cobalt, and Nickel)

Extraction of impurities was performed using the precious metal extraction agent of the example of the present invention.

Several types of acid solutions of sulphuric acid comprising nickel, cobalt, and manganese each in an amount of $1 \times 10^{-4}$ mol/l and being adjusted to pH 2.5 to 7.5, and an equal volume of an N-dodecane solution comprising 0.01 mol/l of a valuable metal extraction agent were added together in test tubes, and the test tubes were put into a constant temperature oven at 25° C. and shaken for 24 hours. At this time, the pH of the sulphuric acid solution was adjusted using 0.1 mol/l sulphuric acid, ammonium sulphate and ammonia.

Figure 5:
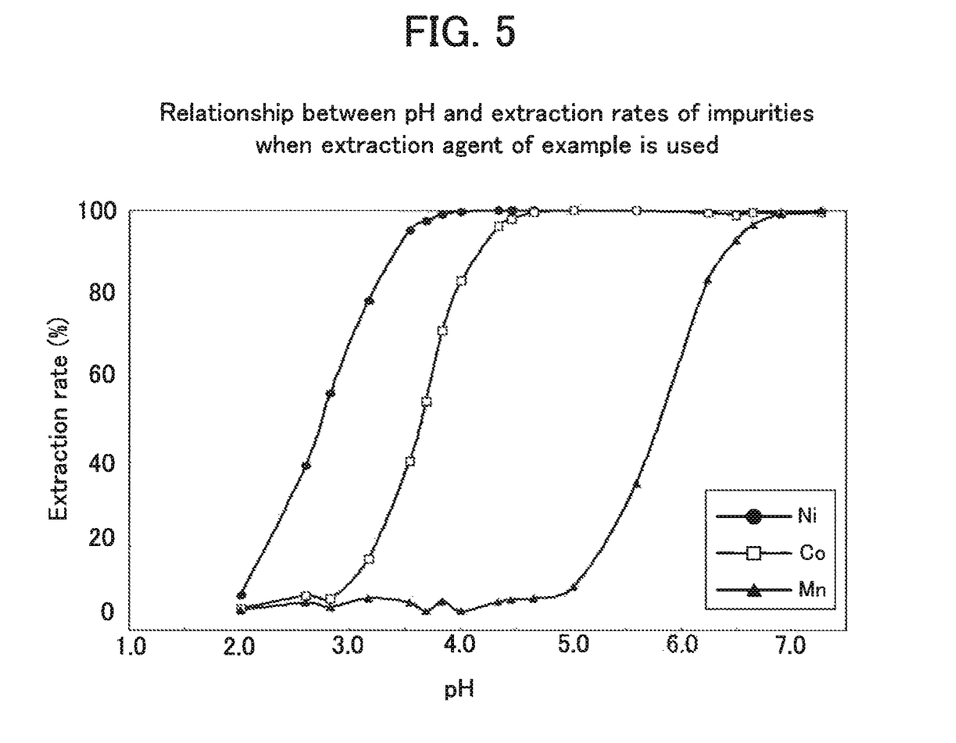
FIG. 5 shows the results of extraction of impurities from an acid solution containing the impurities with the use of a precious metal extraction agent of the example of the present invention.

After shaking, the aqueous phase was collected, and the cobalt concentration and the manganese concentration were measured using inductively coupled plasma-atomic emission spectroscopy (ICP-AES). The organic phase was subjected to back extraction using 1 mol/l sulphuric acid. The nickel concentration, the cobalt concentration, and the manganese concentration in the back extraction phase were measured using ICP-AES. From these measurement results, the extraction rates of nickel, cobalt, and manganese were defined as the amount of material in the organic phase/(the amount of material in the organic phase+the amount of material in the aqueous phase) and measured. The results obtained with the use of the valuable metal extraction agent of the example of the present invention are shown in FIG. 5. In FIG. 5, the abscissa is the pH of an acid solution of sulphuric acid, and the ordinate is the extraction rate (unit: %) of nickel, cobalt, or manganese. In the graphs, circles indicate the extraction rate of nickel, squares indicate the extraction rate of cobalt, and triangles indicate the extraction rate of manganese.

When the precious metal extraction agent of the example of the present invention is used, manganese is not extracted at a pH between a highly acidic region of about 0.8 and a weakly acidic region of 3.5 or higher. Cobalt is not extracted at pH 3.0 or lower, and the pH is more preferably 2.5 or lower. Nickel is not extracted at pH 2.5 or lower, and the pH is more preferably 2.0 or lower. Taking advantage of these extraction properties, it is possible, for example, to extract, separate, and retrieve precious metals directly from an acid solution in which electronic material scrap is dissolved and that has a high concentration, and then retrieve manganese, cobalt, and nickel from the extraction residue. In this way, precious metals can be retrieved with great efficiency.

The invention claimed is:

1. An extraction method for metals, the method comprising subjecting an acid solution containing one or more metals selected from precious metals and rhenium to solvent extraction with a metal extraction agent to extract the one or more metals selected from the precious metals and the rhenium from the acid solution,
   wherein the metal extraction agent that comprises an amide derivative represented by the following general formula (I):

wherein, $R^1$ and $R^2$ each represent the same or different alkyl groups;
the alkyl group can be a straight chain or a branched chain;
$R^3$ represents a hydrogen atom or an alkyl group; and
$R^4$ represents a hydrogen atom or any group other than an amino group, which is bound to the α carbon as an amino acid.

2. The extraction method for metals according to claim 1, wherein the acid solution is subjected to the solvent extraction with the pH of the acid solution adjusted to 3.5 or lower.

3. The extraction method for metals according to claim 1, wherein the acid solution contains the one or more metals selected from the precious metals and the rhenium and at least one or more of manganese, nickel, and/or cobalt, and the acid solution is subjected to the solvent extraction with the pH of the acid solution adjusted to 2.5 or lower.

4. The extraction method according to claim 1, wherein the amide derivative is any one or more of glycinamide derivatives, histidinamide derivatives, lysinamide derivatives, aspartamide derivatives, and N-methylglycine derivatives.

5. A palladium separation method, the method comprising:

subjecting a first acid solution containing palladium and one or more other metals selected from precious metals and rhenium to solvent extraction with a metal extraction agent to extract the palladium and the one or more metals from the acid solution, separating the extraction agent in which the palladium and the other metals have been extracted from the acid solution, adding a second acid solution to the extraction agent in which the palladium and the other metals have been extracted to carry out back extraction, wherein the second acid solution has a pH lower than the pH of the first acid solution, and separating the extraction agent from the second acid solution to separate palladium from the other metals, wherein the metal extraction agent that comprises an amide derivative represented by the following general formula (I):

(I)

wherein, $R^1$ and $R^2$ each represent the same or different alkyl groups;

the alkyl group can be a straight chain or a branched chain;

$R^3$ represents a hydrogen atom or an alkyl group; and $R^4$ represents a hydrogen atom or any group other than an amino group, which is bound to the α carbon as an amino acid.

6. The extraction method according to claim 5, wherein the amide derivative is any one or more of glycinamide derivatives, histidinamide derivatives, lysinamide derivatives, aspartamide derivatives, and N-methylglycine derivatives.

7. A rhenium separation method, the method comprising:

subjecting a first acid solution containing rhenium and one or more other metals selected from precious metals to solvent extraction with a metal extraction agent to extract the rhenium and the one or more metals from the acid solution, separating the extraction agent in which the rhenium and the other metals have been extracted from the acid solution, adding a second acid solution to the extraction agent in which the rhenium and the other metals have been extracted to carry out back extraction, wherein the second acid solution has a pH lower than the pH of the first acid solution, and separating the extraction agent from the second acid solution to separate the rhenium from the precious metals, wherein the metal extraction agent that comprises an amide derivative represented by the following general formula (I):

(I)

wherein, $R^1$ and $R^2$ each represent the same or different alkyl groups;

the alkyl group can be a straight chain or a branched chain;

$R^3$ represents a hydrogen atom or an alkyl group; and $R^4$ represents a hydrogen atom or any group other than an amino group, which is bound to the α carbon as an amino acid.

8. The extraction method according to claim 7, wherein the amide derivative is any one or more of glycinamide derivatives, histidinamide derivatives, lysinamide derivatives, aspartamide derivatives, and N-methylglycine derivatives.

9. A rhodium separation method, the method comprising subjecting an acid solution containing rhodium and at least one or more of platinum, osmium, iridium, and palladium to solvent extraction with a metal extraction agent with the pH of the acid solution adjusted to 2.5 or lower, to separate the rhodium from other metals, wherein the metal extraction agent that comprises an amide derivative represented by the following general formula (I):

(I)

wherein, $R^1$ and $R^2$ each represent the same or different alkyl groups;

the alkyl group can be a straight chain or a branched chain;

$R^3$ represents a hydrogen atom or an alkyl group; and $R^4$ represents a hydrogen atom or any group other than an amino group, which is bound to the α carbon as an amino acid.

10. The extraction method according to claim 9, wherein the amide derivative is any one or more of glycinamide derivatives, histidinamide derivatives, lysinamide derivatives, aspartamide derivatives, and N-methylglycine derivatives.

11. An iridium separation method, the method comprising:

subjecting a first acid solution containing iridium and at least one or more of osmium and ruthenium to solvent extraction with a metal extraction agent, adding, thereto, a second acid solution to form a combined acid solution, wherein the pH of the combined acid solution is adjusted to 1.5 or lower, mixing the combined acid solution to carry out back extraction, and separating the extraction agent from the combined acid solution to separate the iridium from the osmium and the ruthenium, wherein the metal extraction agent that comprises an amide derivative represented by the following general formula (I):

wherein, $R^1$ and $R^2$ each represent the same or different alkyl groups;

the alkyl group can be a straight chain or a branched chain;

$R^3$ represents a hydrogen atom or an alkyl group; and $R^4$ represents a hydrogen atom or any group other than an amino group, which is bound to the α carbon as an amino acid.

12. The extraction method according to claim 11, wherein the amide derivative is any one or more of glycinamide derivatives, histidinamide derivatives, lysinamide derivatives, aspartamide derivatives, and N-methylglycine derivatives.

* * * * *